United States Patent [19]

Becker et al.

[11] Patent Number: 4,502,861

[45] Date of Patent: Mar. 5, 1985

[54] STORAGE STABLE MOTHPROOFING FORMULATIONS

[75] Inventors: Carl Becker; Fritz Heizler, both of Basel, Switzerland

[73] Assignee: Ciba-Geigy Corporation, Ardsley, N.Y.

[21] Appl. No.: 411,163

[22] Filed: Aug. 25, 1982

[30] Foreign Application Priority Data

Sep. 3, 1981 [CH] Switzerland ........................ 5686/81

[51] Int. Cl.$^3$ ............................................ A01N 43/54

[52] U.S. Cl. ........................................ 8/490; 252/8.8; 427/389

[58] Field of Search ................. 8/490; 427/389, 389.9, 427/392; 424/186, 187, 254; 252/8.6, 8.8, 8.7, 8.9

[56] References Cited

U.S. PATENT DOCUMENTS 4,283,444 8/1981 de Sousa et al. .................... 427/421

*Primary Examiner*—Michael R. Lusignan

*Attorney, Agent, or Firm*—Edward McC. Roberts

[57] ABSTRACT

The invention provides storage stable formulations of mothproofing compositions which contain a 5-phenylcarbamoylbarbituric acid and a synthetic pyrethroid as active ingredients and, as formulation components, aliphatic or cycloaliphatic amines or amides or derivatives thereof, and, if appropriate, organic solvents and water, surfactants, emulsifiers and/or dispersants, and optionally aliphatic carboxylic acids. The invention further relates to a process for the preparation of these formulations and to a method of using said formulations for providing keratinous material, in particular wool textiles, with a protective finish against attack by pests that feed on keratin.

26 Claims, No Drawings

STORAGE STABLE MOTHPROOFING FORMULATIONS

The present invention relates to a storage stable formulation of a mothproofing composition and to a method of providing keratinous material with a mothproof and beetle-resistant finish, which method comprises the use of the said formulation.

It is known from German Offenlegungsschrift No. 2 936 457 that 5-phenylcarbamoylbarbituric acid compounds are very effective against pests that feed on keratin. Combinations of these 5-phenylcarbamoylbarbituric acid compounds and synthetic pyrethroids are particularly suitable for proofing keratinous material, especially wool, furs and feathers, against attack by larvae that feed on keratin, for example against the larvae of the webbing clothes moth (Tineola bisselliella), of the common clothes moth (Tinea pellionella), of the false clothes moth (Hofmannophila pseudopretella), of the fur beetle (Attagenus piceus) and of the carpet beetle (Anthrenus vorax). If combinations of the cited active ingredients are applied e.g. in conventional manner to woollen articles, these latter are very well protected against the above pests. Despite the known excellent properties of the active ingredient combination referred to above, it has so far not been possible to introduce an appropriate mothproofing agent onto the market, as no formulation of the active ingredients has been found which has an adequate storage stability, which can readily be diluted with water to give a treatment bath, and which meets all other requirements made of such formulations (see below). A particular problem has been the exceedingly low water solubility of the barbituric acid component.

Accordingly, it is the object of the present invention to provide a formulation of a mothproofing combination composition comprising a 5-phenylcarbamoylbarbituric acid component and a pyrethroid component, which formulation shall remain storage stable over a prolonged period of time (i.e. without the occurrence of precipitation or demixing), be as far as possible colourless, and be miscible with water. Furthermore, this formulation shall not have any deleterious effect on handle, shade and colour fastness when applied to wool, it shall be applicable in classical continuous dyeing and after-treatment processes and also applicable together with conventional textile finishing agents (e.g. wool levelling agents) without having any adverse effects thereon, and it shall have low toxicity and be readily biodegradable.

Surprisingly, it has now been found that a formulation having all the required properties may be obtained by mixing the two active components with specific aliphatic nitrogen-containing compounds, if appropriate together with an organic solvent, water, surfactants and/or emulsifiers or dispersants.

The formulation of the present invention comprises

A. a 5-phenylcarbamoylbarbituric acid compound of the general formula

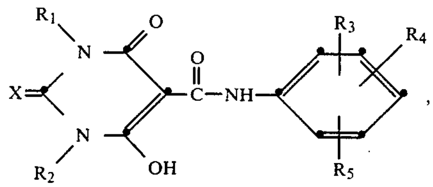

(1)

wherein X is oxygen or sulfur, each of $R_1$ and $R_2$ independently of the other is alkyl of 1 to 4 carbon atoms, alkenyl of 3 or 4 carbon atoms, benzyl, phenyl or substituted phenyl, $R_3$ is halogen, nitro or trihalomethyl, $R_4$ is hydrogen, halogen or trihalomethyl, and $R_5$ is hydrogen, halogen, methyl or methoxy, or a tautomer or salt thereof.

B. a synthetic pyrethroid of the general formula

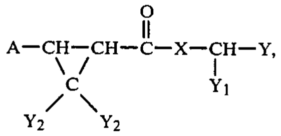

(2)

wherein A is $Br_2C{=}CBr$—, 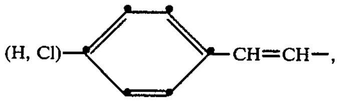

Cl—C≡C—, 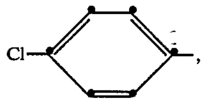

$(CH_3)_3C$—O—, 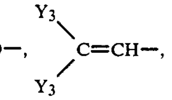

wherein Y is Cl, Br, $CF_3$, F or methyl, $CH_2{=}CH{-}CH_2{-}O{-}$ or

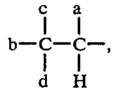

wherein each of a, b, c and d independently of one another is Cl, Br or F, and c and d may also be methyl, X is oxygen or sulfur, $Y_1$ is hydrogen, CN, $CH_3$, $C_2H_5$, i-$C_3H_7$,

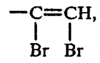

—C≡CH, —C≡C—$CH_3$, —C≡C—$C_6H_5$, —CH=CH—$CH_3$, —$CH_2$—CH=$CH_2$, —CH=$CH_2$ or —$CH_2$—CH=CHCl, $Y_2$ is methyl or both $Y_2$'s together complete a cyclopropane, cyclobutane or cyclopentane ring, and Y is

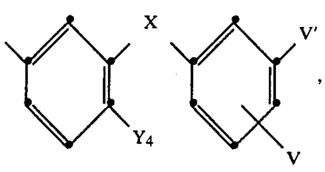

wherein $Y_4$ is hydrogen or fluorine and V is hydrogen, Cl, Br, F, $CH_3$ or $NO_2$, or V' may be $CF_3$ if V is hydrogen, and X is as defined above; and Y is also

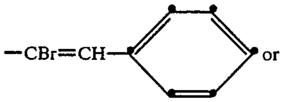 or

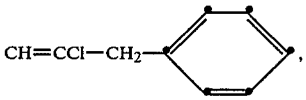,

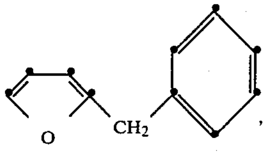,

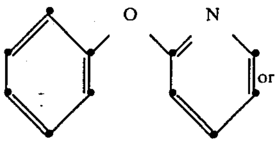 or 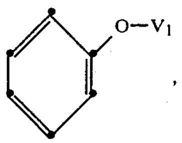, wherein $V_1$ is $—CH_2—CH=CH_2$, $—CH_2—CH≡CH$, $—CH_2—CH=CH—CH_3$,

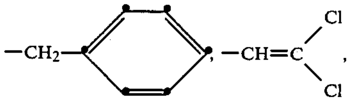, $—CF=CFCl$ or $—CF=CF_2$,

C. one or more aliphatic or cycloaliphatic amines and/or amides or derivatives thereof, D. optionally one or more organic solvents, E. optionally water, provided the organic solvent D is present and is miscible with water, F. optionally one or more surfactants and/or emulsifiers or dispersants which differ from component C, and G. optionally one or more aliphatic carboxylic acids.

The formulations of this invention comprise e.g. (percentages are by weight, in each case based on the entire formulation)

0.5 to 20%, preferably 1 to 15%, e.g. 1 to 10%, and most preferably 4 to 6%, of component A,
0.5 to 20%, preferably 1 to 15%, e.g. 1 to 10%, and most preferably 4 to 6%, of component B,
1 to 90%, preferably 5 to 60%, most preferably 10 to 50%, e.g. 15 to 35%, of component C,
0 to 80%, preferably 10 to 80%, most preferably 15 to 75%, of component D,
0 to 40% of component E,
0 to 30%, e.g. 5 to 15%, of component F, and
0 to 10%, e.g. 1 to 5%, of component G.

The ratio of the two components A and B may be e.g. from 1:4 to 4:1, preferably from 1:2 to 2:1. In particularly preferred formulations this ratio is about 1:1.

The amount of nitrogen-containing component C in the formulation depends primarily on the amount of component A. The ratio of A:C may be e.g. from 1:0.2 to 1:20, in particular from about 1:1 to 1:8, and most preferably from 1:1 to 1:6, e.g from 1:3 to 1:5.

The amount of component D (organic solvent), provided one is present in the formulation, depends on the amount of component C, on the nature of the solvent, and also on whether the formulation also contains water (if the solvent is miscible with water).

In formula (1) above, which encompasses the possible components A, those compounds are preferred in which X is oxygen. If in formula (1) a phenyl radical $R_1$ or $R_2$ is substituted, it carries preferably one to three substituents selected from the group consisting of alkyl or alkoxy, each of 1 to 4 carbon atoms, chlorine, bromine, fluorine, nitro or trihalomethyl, but at most one nitro group and at most two trihalomethyl and alkoxy groups. Halogen denotes all halogen atoms, with chlorine, bromine or fluorine being preferred.

Particularly interesting compounds for use as component A are compounds of the general formula

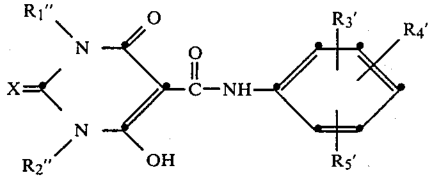 (3)

wherein X is oxygen or sulfur, each of $R_1''$ and $R_2''$ independently of the other is methyl, ethyl, allyl or a group of the formula

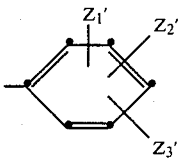

wherein $Z_1'$ is hydrogen, chlorine, bromine, methyl, methoxy, ethoxy, $—CF_3$ or nitro, $Z_2'$ is hydrogen, chlorine, bromine, methyl or $—CF_3$, $Z_3'$ is hydrogen, chlorine or methyl, $R_3'$ is chlorine, bromine or $—CF_3$, $R_4'$ is hydrogen, chlorine or bromine, and $R_5'$ is hydrogen, chlorine, bromine, methyl or methoxy, and the tautomers and salts thereof.

Within the scope of the formula (3), preferred compounds are those in which $R_1''$ and $R_2''$ are the same, in particular those in which $R_1''$ and $R_2''$ are methyl, $R_3'$ is $—CF_3$, chlorine or bromine, $R_4'$ is chlorine or hydrogen and $R_5'$ is hydrogen, and X is oxygen.

The compounds of formula (1) and (3) are obtained in different tautomeric forms (keto-enol tautomerism). Possible resonance structures are cited in U.S. Pat. No. 4,283,444. Each of the possible tautomeric forms may be employed in the formulations of this invention.

The compounds of formula (1) and (3) may also be used in the form of their salts. Among the salts, the alkali metal salts, ammonium salts or amine salts may be especially mentioned, with sodium, potassium, ammonium or alkylamine salts, in particular triethylamine salts, being preferred.

As preferred components B there may be used those of the above defined formula (2), wherein A is a radical of the formula

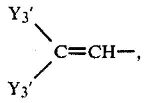

wherein $Y_3'$ is bromine, chlorine or methyl, X is oxygen and Y is

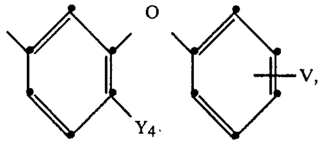

preferably

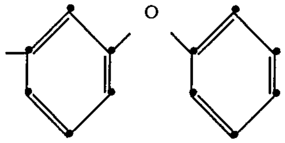

$Y_2$ in formula (2) is preferably methyl and $Y_1$ is hydrogen, CN, $CH_3$, $-CH{=}CH_2-$ or $-C{\equiv}CH-$, in particular hydrogen or CN.

In useful formulations, component B is a compound of the class of the 3″-phenoxybenzyl 3-(2′,2′-dihalovinyl)-2,2-dimethylcyclopropanecarboxylates, in particular one of the two compounds.

(4)

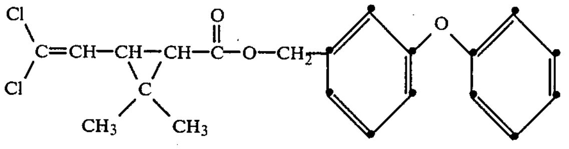

and (5)

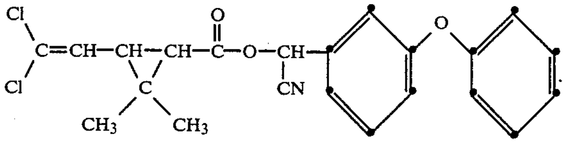

The trivial name of compound (4) is permethrin and that of compound (5) is cypermethrin. These two names are used throughout this specification.

Component C in the formulations of this invention is an aliphatic or cycloaliphatic amine or amide or a derivative thereof. More than one of these nitrogen-containing compounds may also be present in the formulation.

Examples of compounds suitable for use as component C comprise: primary, secondary or tertiary aliphatic saturated or unsaturated acyclic or cyclic amines; quaternisation products of these tertiary amines; amine oxides; alkoxylation products of these amines, including reaction products of these alkoxylated amines with various acids (esters); amino alcohols and their alkoxylation products; alkylpropylenediamines; amides of carboxylic acids and alkoxylation products thereof; alkoxylated carboxylic acid alkylolamides.

The above acyclic amines and amides and derivatives thereof (especially alkoxylation products) preferably have at least one long hydrocarbon chain, e.g. one containing 8 to 22, preferably 10 to 20, most preferably 10 to 18, carbon atoms. The amines and amine oxides are therefore preferably fatty amines and oxides thereof and the amides are derived from fatty acids. Examples of primary amines are: decylamine, laurylamine, cocoylamine, tallow fatty amine, octadecylamine, oleylamine. Examples of secondary amines are: $C_1$-$C_4$alkyl fatty amines, e.g. methyl laurylamine or ethyl laurylamine, ethyl cocoylamine or methyl cocoylamine, methyl or ethyl tallow fatty amine. Examples of tertiary amines are: dimethyl or diethyl laurylamine, dimethyl or diethyl cocoylamine, dimethyl or diethyl tallow fatty amine. Examples of quaternised amines are: quaternisation products of these last mentioned tertiary amines, e.g. with dimethyl sulfate or methyl iodide. Examples of amine oxides are those obtained by known oxidation from the above specified primary, secondary and tertiary amines. Examples of fatty acid amides are lauryl amides, coconut fatty acid amides, tallow fatty acid amides and other fatty acid amides. These amides may be reacted with an alkylene oxide to give the corresponding alkoxylated fatty acid amides. Amino alcohols and their reaction products with alkylene oxides also contain a long hydrocarbon chain of the lengths stated above. Among the above mentioned alkoxylation products, propoxylation products are preferred, with ethoxylation products being especially preferred.

Suitable cyclic primary, secondary or tertiary amines which may be used in the formulations of the invention are e.g. those based on pyrrolidine, pyrroline, pyrazoline, pyrazolidine, imidazoline, imidazolidine, piperidine or piperazine. These cyclic amines are preferably additionally substituted by a long chain hydrocarbon radical containing 8 to 22, preferably 10 to 18, carbon atoms. Examples of such amines are 1-$C_1$-$C_4$alkyl-2-$C_8$-$C_{22}$alkyl or -$C_8$-$C_{22}$alkenylimidazoline, in which the lower alkyl moiety may additionally be substituted, e.g. by hydroxy.

Suitable alkoxylation products of fatty amines are, for example, those of the formula

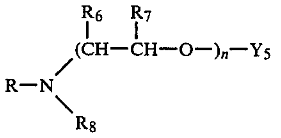

(6)

wherein R is a $C_8$-$C_{22}$alkyl or $C_8$-$C_{22}$alkenyl radical, each of $R_6$ and $R_7$ independently of the other is hydrogen or a methyl group, n is an integer from 1 to 100, preferably from 1 to 30, $Y_5$ is hydrogen or the radical of an acid, e.g. of phosphoric acid or of sulfuric acid, e.g. a $-SO_3M-$ group, in which M is hydrogen or an alkali metal ion or an ammonium ion, $R_8$ is hydrogen, a $C_1$-$C_4$alkyl radical, the grouping

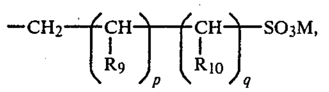

in which each of $R_9$ and $R_{10}$ independently of the other is hydrogen or a hydroxyl group, and the sum of p+q is 1 to 3, or the grouping

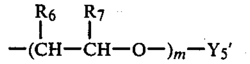

wherein $Y_5'$ is the same as $Y_5$, and $Y_5$ and $Y_5'$ together may also be the radical of an acid, e.g. of phosphoric acid, and m is an integer from 1 to 100, preferably from 1 to 30, and the sum of n+m is preferably 2 to 50, in particular 2 to 30, and the quaternisation products thereof if $R_8$ is not hydrogen.

The quaternisation products may be obtained in known manner from the non-quaternised compounds of formula (6) by reaction with conventional quaternising agents. These quaternisation products have e.g. the formula (7)

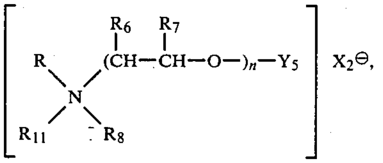

wherein R, $R_6$, $R_7$, $R_8$, n and $Y_5$ are as defined for formula (6) and $R_{11}$ is a $C_1$–$C_8$alkyl group which is unsubstituted or substituted by a hydroxyl or carboxamide group, or is a benzyl radical or the grouping

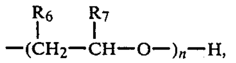

wherein $R_6$ and $R_7$ are as defined above, and $X_2^{\ominus}$ is an anion. R as a $C_8$–$C_{22}$alkyl radical may be e.g. the dodecyl, tetradecyl, hexadecyl, octadecyl, tallyl, cocoyl or docosyl radical, and R as a $C_8$–$C_{22}$alkenyl radical may be the tetradecenyl, hexadecenyl, oleyl or octadecenyl radical.

Suitable alkali metal atoms M are in particular the sodium or potassium atom, and the ammonium group is the ammonium group itself and the ammonium groups derived from mono-, di- or triethanolamine.

$R_{11}$ as a $C_1$–$C_8$alkyl radical which is unsubstituted or substituted by a hydroxyl or carboxamide group may be e.g. the methyl, ethyl, isopropyl or secondary butyl group or the carboxamidomethyl, 2hydroxyethyl and 1-hydroxyprop-2-yl group.

Suitable anions $X_2^{\ominus}$ are in particular halide ions such as the chloride, bromide or iodide ions of acidic alkylsulfuric acid esters such as the methylsulfate and ethylsulfate ion, and the toluenesulfonic acid ion.

Within the scope of formula (6) it is preferred to use oxalkylation products of fatty amines of the formula (8)

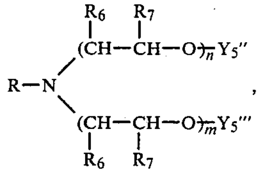

wherein R, $R_6$, $R_7$, n and m are as defined for formula (6), and each of $Y_5''$ and $Y_5'''$ independently of the other is hydrogen or the —$SO_3M$ group, wherein M is as defined for formula (6); and, in particular, those of the formula (9)

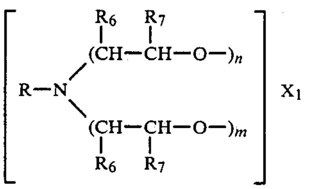

or the alkali metal salts, ammonium salts or amine salts thereof, wherein R, $R_6$, $R_7$, n and m are as defined for formula (6) and $X_1$ is the acid radical of phosphoric acid, the acid hydrogen atoms of which radical may be replaced by alkali metal ions, ammonium ions or amine salt ions.

The alkyl or alkenyl radical R in formulae (8) and (9) preferably contains 10 to 18 carbon atoms and the sum of n+m is 4 to 20, in particular 6 to 8. $R_6$ and $R_7$ are preferably hydrogen. In formula (8), $Y_5''$ and/or $Y_5'''$ are preferably a —$SO_3M$ group, in which M is hydrogen or an alkali metal ion or ammonium ion.

In general, the radical R must not contain a specific number of carbon atoms but may also be a mixture of different long chain hydrocarbon radicals, as is the case with many fatty amines which are derived from natural fats. A preferred radical of this kind is the hydrocarbon radical of tallow fatty amine or of coconut fatty amine. A further preferred radical is the lauryl radical.

The acid component of the ester of formula (9) is phosphoric acid, $X_1$ is therefore the radical of phosphoric acid, wherein the terminal OH groups of the ethylene oxide chains may be completely or only partially esterified. The number of acid hydrogen atoms in the phosphoric acid radical depends on the degree of esterification, which must not be a whole number. These acid hydrogen atoms may also be replaced by alkali metal ions or ammonium ions, so that the radical $X_1$ exists in salt form.

Depending on the degree of esterification, possible structures of compounds of formula (9) would be e.g. the following (for $R_6$=$R_7$=H):

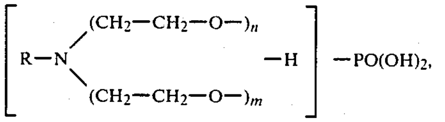

-continued

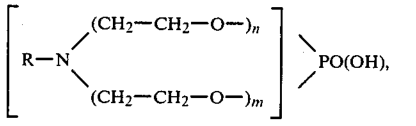

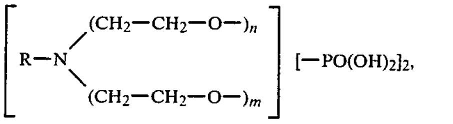

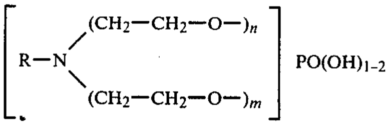 etc.

The oxethylation products of fatty amines described above, e.g. those of the formulae (6) to (9), are known, e.g. from German Offenlegungsschrift specification Nos.2 412 785 and 2 928 052 and from European patent application No. 32 483.

As organic solvents (component D) in the formulations of the invention there may be used polar and nonpolar, protic or aprotic, water-miscible or water-immiscible organic solvents. Typical examples of such solvents are: aliphatic, cycloaliphatic or aromatic hydrocarbons, e.g. various petroleum fractions, cyclohexane, benzene, toluene, xylenes, various naphtha and paraffin fractions; aliphatic and alicyclic mono- or polyfunctional alcohols such as ethanol, methanol, isopropanol, ethylene glycol, propylene glycol, cyclohexanol, benzyl alcohol; ketones such as methyl ethyl ketone, and cyclic ketones such as cyclohexanone, 3,5,5-trimethylcyclohexen-1-one (isophoron); chlorinated and fluorinated aliphatic or aromatic hydrocarbons such as dichloroethane, dichloroethylene, trichloroethylene or trichloroethane, chloroform, carbon tetrachloride, perchloroethylene, chlorobenzene, dichlorobenzene, trichlorobenzenes; ethers such as methoxyethanol, ethoxyethanol, acetoxy-2-ethoxyethane, dioxan; and also dimethyl formamide, formamide, dimethyl sulfoxide, dimethyl methylphosphonate (DMMP), N-methylpyrrolidone; glycol ethers such as ethyl glycol, methyl glycol, polyethylene glycols, ethylene glycol alkyl ethers, tri- or diethylene glycol alkyl ethers, ethyl polyglycol, e.g. mixtures of monoethylene glycol ethyl ether, diethylene glycol ethyl ether, triethylene glycol ethyl ether and polyethylene glycol ethyl ether; polydiols; terpene hydrocarbons, e.g. pine oil.

Preferred solvents are: dimethyl methylphosphonate, acetoxy-2-ethoxyethane, N-methylpyrrolidone, ethylene glycol, mono-, di-, tri- and polyethylene glycol ethyl ethers and mixtures thereof, e.g. ethyl polyglycol, isoparaffin, isophoron, benzene, xylene, toluene, naphtha, polydiols, pine oil etc.

The surfactants, emulsifiers or dispersants (component F) in the formulations of the invention differ from the nitrogen-containing component C and may belong to the known classes of surfactants, emulsifiers or dispersants. Typical examples are: block polymers of propylene glycol and ethylene oxide of the general formula $$HO(C_2H_4O)_x—(C_3H_6O)_y—(C_2H_4O)_zH \quad (10)$$

and having a molecular weight of 2000 to 20,000, wherein the ethylene oxide content (x+z) is 10 to 85% by weight and the propylene oxide content (y) is 15 to 90% by weight; ethoxylated fatty alcohols, e.g. those of the formula $H(C_2H_4O)_{a'}—OR^2$, wherein a' is preferably a number from 10 to 200, $R^2$ is an alkyl, cycloalkyl or alkenyl radical containing 8 to 22 carbon atoms or a phenylalkyl radical; ethoxylated alkylphenols, for example those of the formula

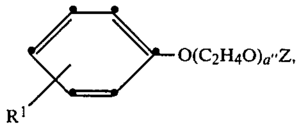

(11)

wherein $R^1$ is alkyl of 6 to 18 carbon atoms, Z is hydrogen, $—SO_3M$ or $—PO_3M$, in which M is hydrogen, an alkali metal ion or an ammonium ion and a'' is an integer from 4 to 50; also polyvinyl alcohols, polyvinyl pyrrolidones; polyethylene glycols, cellulose ethers, ethoxylated fatty acids, N-allylated amino fatty acids, alkylphosphoric acid partial esters, salts of higher derivatives of sulfur oxyacids (e.g. the sodium salt of dodecylbenzenesulfuric acid, water-soluble salts of sulfuric acid monoesters of higher molecular alcohols or their polyglycol ethers, e.g. soluble salts of dodecyl alcohol sulfate or of dodecyl alcohol polyglycol ether sulfate), derivatives of phosphorus oxyacids (e.g. phosphates), onium compounds, polyhydroxy compounds, surfactants based on mono- or polysaccharides, higher molecular acetylene glycols, polyglycol ethers (e.g. polyglycol ethers of higher fatty alcohols, polyglycol ethers of higher molecular alkylated phenols), sulfated castor oil, fatty alcohol sulfates, alkylsulfonates, soluble salts of sulfonic acid hemiesters of higher fatty alcohols, higher and/or polyalkylated arylsulfonic acids; sulfocarboxylic acid esters of average to higher alcohols, fatty acid acylaminoalkyl or aminoaryl glycerol sulfonates, phosphoric acid esters of fatty alcohols, alkylbenzenesulfonates, paraffin sulfonates, α-olefinsulfonates, α-sulfocarboxylic acids and salts and esters thereof, alkylglyceryl ether sulfonates, fatty acid monoglyceride sulfates and sulfonates, 2-acyloxyalkanesulfonates, β-alkyloxyalkanesulfonates, polypropoxyglycols, phosphine oxides, sulfoxides and N,N-dialkylaminocarboxylic acids.

Preferred surfactants, dispersants and emulsifiers are: block polymers of propylene glycol and ethylene oxide (see also formula 10 above), polyglycol ethers of higher fatty alcohols, ethoxylated alkylphenols (alkylphenol polyglycol ethers) and esters thereof with acids, e.g. the corresponding sulfates and phosphates (see also formula II above), ethoxylated fatty alcohols, ethoxylated cyclic alcohols, alkylphosphoric acid partial esters, N,N-dialkylaminocarboxylic acids and polyethylene glycol.

Suitable aliphatic carboxylic acids which may optionally be present in the formulations of the invention as component G are preferably saturated or unsaturated monocarboxylic acids, dicarboxylic acids or hydroxymono- or hydroxydicarboxylic acids. Examples of such acids are: formic acid, acetic acid, propionic acid, butyric acid, valeric acid and long chain monocarboxylic acids, oxalic acid, malonic acid, maleic acid, fumaric acid, glutaric acid, adipic acid, tartaric acid, malic acid, citric acid, succinic acid, lactic acid etc. Preferred carboxylic acids are formic acid, acetic acid, succinic acid and lactic acid.

The formulations of the invention may optionally also contain additional components, e.g. those which further improve the properties of the formulation itself and/or facilitate application and/or still further increase the efficacy of the active ingredient combination. An example of such additional components is piperonyl butoxide, which effects even better protection of the substrates treated with the formulations of this invention. For example, the formulations may contain piperonyl butoxide (=(3,4-methylenedioxy-6-propylbenzyl)-butyl-diethylene glycol ether) in an amount of 5 to 40%.

Preferred formulations, in which the components are dissolved, have e.g. the following composition:

A. 1 to 15% of a 5-phenylcarbamoylbarbituric acid of the formula (3), preferably one in which X is oxygen, $R_3'$ is $CF_3$, Cl or Br, $R_4'$ is Cl or hydrogen, $R_5'$ is hydrogen and $R_1''$ and $R_2''$ are the same, B. 1 to 15% of a synthetic pyrethroid of the formula (12)

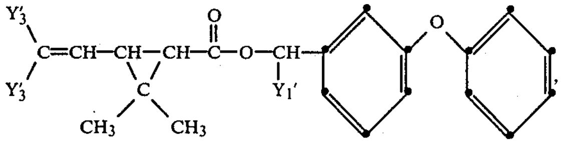

wherein $X_1'$ is hydrogen, CN, $CH_3$, $—CH{=}CH_2—$ or $C{\equiv}CH$ and $Y_3'$ is Br, Cl or $CH_3$, C. 5 to 60% of a primary, secondary or tertiary fatty amine or fatty amine oxide, of a free or ethoxylated fatty acid amide, of a quaternary fatty amine, of a cyclic amine which is substituted by a $C_8$–$C_{22}$alkyl or $C_8$–$C_{22}$alkenyl group, of an ethoxylated fatty acid alkylolamide, of an alkylpropylenediamine, of an ethoxylated amino alcohol or of an ethoxylated primary, secondary, tertiary or quaternary fatty amine, in particular one of the formula (6), or of a mixture of several of the above nitrogen-containing compounds, D. 15 to 75% of one or more organic solvents, E. 0 to 40% of water, provided component D is a water-miscible organic solvent.

F. 0 to 15% of a surfactant and/or emulsifier and/or dispersant or of a mixture of several such compounds, and G. 0 to 5% of a saturated or unsaturated mono- or dicarboxylic acid or of a hydroxymono- or hydroxydicarboxylic acid.

Particularly useful formulations comprise

A. 1 to 10% of a 5-phenylcarbamoylbarbituric acid of the formula (3), wherein X is oxygen, $R_1''$ and $R_2''$ are methyl, $R_3'$ is chlorine, $R_4'$ is hydrogen or chlorine and $R_5'$ is hydrogen, B. 1 to 10% of a synthetic pyrethroid of the formula (12), wherein $Y_1'$ is hydrogen or cyano and $Y_3'$ is chlorine, C. 10 to 50% of a primary, secondary or tertiary fatty amine or of a fatty amine oxide, of a quaternary fatty amine, of a 1-($C_1$–$C_4$)alkyl- or -($C_1$–$C_4$)hydroxyalkyl-2-($C_8$–$C_{22}$)alkyl- or -($C_8$–$C_{22}$)alkenylimidazoline or of an ethoxylated fatty amine of the formula (8) or (9), or of a mixture of the above nitrogen-containing compounds, D. 15 to 75% of one or more solvents selected from the group consisting of dimethyl methylphosphonate, acetoxy-2-ethoxyethane, N-methylpyrrolidone, ethylene glycol, mono-, di-, tri- and polyethylene glycol ethyl ethers and mixtures thereof, e.g. ethyl polyglycol, isoparaffins, isophoron, benzene, xylene, toluene, naphtha, polydiols and pine oil, E. 0 to 40% of water, provided component D is a water-miscible solvent, F. 0 to 15% of a surfactant, dispersant or emulsifier selected from the group consisting of: block polymers of propylene glycol and ethylene oxide, polyglycol ethers of higher fatty alcohols, ethoxylated alkylphenols and esters thereof with acids, e.g. the corresponding sulfates and phosphates, ethoxylated fatty alcohols, ethoxylated cyclic alcohols, alkylphosphoric acid partial esters, N,N-dialkylaminocarboxylic acids and polyethylene glycol, and G. 0 to 5% of a carboxylic acid selected from the group consisting of: formic acid, acetic acid, propionic acid, butyric acid, valeric acid and long chain monocarboxylic acids, oxalic acid, malonic acid, maleic acid, furmaric acid, glutaric acid, adipic acid, tartaric acid, malic acid, citric acid, succinic acid and lactic acid.

The preparation of the above formulations may be effected in principle by adding the components in any order and thoroughly mixing them, if appropriate with gentle heating, until a homogeneous formulation (usually a solution) is obtained. In a preferred embodiment, components B to G are first mixed and then component A is added with efficient stirring, if appropriate at elevated temperature, e.g. in the range from 40° to 70° C. A clear solution is usually obtained immediately by proceeding in this manner.

The mothproofing formulations of the invention may be used for protecting keratinous material from attack by insects that feed on keratin, e.g. Lepidoptera larvae such as Tineola spec. and Tinea spec., and also Coleoptera larvae, e.g. Anthrenus spec. and Attagenus spec. The formulations are most suitable for proofing keratinous material against feeding damage by insects, especially for providing such material with a washfast and lightfast protective finish against insects, in particular moths and beetles. The keratinous material to be proofed can be both in the raw and in the processed state, for example raw or processed sheep's wool or products made of other animal hairs, hides, furs and feathers.

A particularly important feature is the effectiveness of the formulations of this invention against the larvae of the webbing clothes moth (*Tineola bisselliella*), the common clothes moth (*Tinea pellionella*) and of the false clothes moth (*Hofmannophila pseudopretella*), as well as against the larvae of fur beetles and carpet beetles (Attagenus spec. and Anthrenus spec. respectively), e.g. against larvae of *Anthrenus verbasci* and *Anthrenus pimpinellae*, of *Anthrenus scrophilariae*, of *Anthrenus fasciatus*, *Attagenus pellio* and, in particular, of the black fur beetle (*Attagenus piceus*) and of the carpet bug (*Anthrenus vorax*).

The method of the present invention is therefore preferably used on the one hand for protecting woollen textiles, for example blankets, wool carpets, woollen underwear, woollen clothing, knits and wool-containing textiles such as blends, one component of which is wool, for example blends of wool and other natural fibres, preferably cotton, or of wool and synthetic fibres, and, on the other hand, also for protecting furs and skins from attack by the above-mentioned pests.

The method of protecting keratinous material, especially woollen textiles, against the above mentioned pests, comprises preparing a treatment bath from a part of a formulation according to the invention by dilution, to which bath there may be further added conventional textile auxiliaries and/or dyes, and impregnating the material to be protected with this bath.

The textile materials can be impregnated e.g. with hot or cold aqueous dye, bleaching, chroming or aftertreatment baths, whilst various textile finishing methods are possible, for example the pad or exhaust method.

The treatment is conveniently carried out in the temperature range from 10° to 100° C., in the dye bath preferably in the range from about 60° to 100° C. and in the aftertreatment or wash bath preferably in the range from 10° to 70° C., preferably from 20° to 60° C.

As further auxiliaries there may be added to the treatment baths e.g. dispersants, emulsifiers or surfactants, provided the formulation does not already contain these in sufficient amount. The liquor can additionally contain further conventional assistants, such as water-soluble perborates, polyphosphates, carbonates, silicates, fluorescent whitening agents, plasticisers, salts with acid reaction, such as ammonium or zinc silicofluoride, or certain organic acids such as oxalic acid, acetic acid or, in particular, formic acid, and also antimicrobial agents and finishing agents, for example those based on synthetic resins or starch. If the mothproof and beetle-resistant finishing is carried out together with dyeing of the material (e.g. wool), the baths additionally contain the corresponding dyes and, if appropriate, the necessary assistants, e.g. levelling agents.

If non-aqueous application is made (solvent application), an appropriate amount of a formulation may also be added to a suitable solvent and the material to be protected may be impregnated with the solution so obtained. Suitable solvents for this application are, inter alia, trichloroethylene, methylene chloride, hydrocarbons, propylene glycol, methoxyethanol, ethoxyethanol, dimethyl formamide, to which dispersing agents (e.g. emulsifiers, such as sulfated castor oil, fatty alcohol sulfates etc) and/or other assistants can be added. The material to be protected is usually simply impregnated with these solutions.

The proofing of the material to be protected may also be combined with a dry cleaning process. To this end, an appropriate amount of a formulation is dissolved in the cleansing agent (such as a lower halogenated alkane, e.g. trichloroethylene etc.) and the cleaning process is carried out in the usual manner.

However, an amount of the formulation may also be dissolved in a readily volatile organic solvent and the resulting solution then sprayed onto the substrate (spray application). Textile fabrics which contain wool, furs and feathers are particularly suitable for this application. The advantage of the spray application is that pollution of the wastewaters is avoided on account of the recovery of the solvent.

In the method of the present invention, the formulations may also be used in combination with other protectants which act against insects that feed on keratin, for example with urea derivatives, benzimidazoles, aromatic sulfonamides and phosphoric and phosphonic acid esters.

The amount of formulation which is added to the treatment bath or non-aqueous solvent depends on the substrate and the method of application. However, this amount is ordinarily such that, after application to the material which it is desired to protect, the latter contains about 10 to 2000 ppm, preferably 100 to 1000 ppm, of active ingredient, i.e. of barbiturate +pyrethroid (component A+B), with the upper limit being largely determined by economic considerations, whereas the lower limit depends on criteria such as the intended breadth and permanency of the protective action. This corresponds, for example, to concentrations of 0.001 to 1 g of active ingredient per liter of treatment bath, using the exhaust method at a liquor to goods ratio of 1:20, i.e. about 0.005 to 200 g of formulation per liter of treatment bath, depending on the degree of exhaustion attainable. In the pad method, concentrations of up to 400 g of formulation per liter are possible.

In the following Examples parts and percentages are by weight, unless otherwise specified. The names "permethrin" and "cypermethrin" will be understood as meaning the above defined compounds of the formulae (4) and (5).

EXAMPLE 1

A mixture is prepared from 5.5 parts of cypermethrin (cis:trans=35±5%:65±5%),
5.0 parts of tallow fatty amine ethoxylated with 6 to 7 moles of ethylene oxide
25.0 parts of dimethyl laurylamine oxide,
14.5 parts of a block polymer of propylene glycol and ethylene oxide (average mol. wt. 4900; 80% hydrophobic groups, 20% hydrophilic groups; HLB=4),
7.5 parts of castor oil polyglycol ether,
3.0 parts of alkylphenol polyglycol ether phosphate and
34.5 parts of dimethyl methylphosphonate.

With constant stirring, 5 parts of 5-(3,4-dichlorophenyl)carbamoyl-1,3-dimethylbarbituric acid (m.p. 180°–182° C.) are added to this mixture at 45°–55° C. until a homogeneous formulation is obtained. The resultant mothproofing formulation is storage stable, water-miscible, and gives excellent mothproof and beetle-resistant finishes when applied to keratinous material.

In the above formulation, cypermethrin may be replaced by permethrin, dimethyl methylphosphonate by N-methyl-2-pyrrolidone, diethylene glycol ethyl ether, ethyl polyglycol or a polydiol, and/or the alkylphenol polyglycol ether phosphate by succinic acid, lactic acid, formic acid or acetic acid. Formulations with the same good properties are obtained.

The formulations described in the following Examples are obtained as in Example 1, i.e. the components, except the barbituric acid derivative, are mixed and the latter is then added in the manner described. All the formulations so obtained have the required properties, viz. good storage stability, water-miscibility and easy application to keratinous materials.

EXAMPLE 2

A formulation of the following composition is prepared as in Example 1:

5.5 parts of cypermethrin (cis:trans=35±5%:65±5%),
5.0 parts of 5-(3,4-dichlorophenyl)carbamoyl-1,3-dimethylbarbituric acid,
20.0 parts of tallow fatty amine ethoxylated with 6 to 7 moles of ethylene oxide,
10.0 parts of a block polymer of propylene glycol and ethylene oxide (average mol. wt. 4900; 80% hydrophobic groups, 20% hydrophilic groups; HLB=4),
5.0 parts of stearyl alcohol ethoxylated with 8 to 9 moles of ethylene oxide,
1.5 parts of an alkylphosphoric acid partial ester,
53.0 parts of dimethyl methylphosphonate.

In this formulation, cypermethrin may be replaced by permethrin, dimethyl methylphosphonate by 1-acetoxy-2-ethoxyethane, N-methyl-2-pyrrolidone, diethylene glycol ethyl ether, ethyl polyglycol or a polydiol, and/or the alkylphosphoric acid partial ester by succinic acid, lactic acid, formic acid or acetic acid.

EXAMPLE 3

A formulation of the following composition is prepared as in Example 1:
5.5 parts of permethrin,
5.0 parts of 5-(3,4-dichlorophenyl)carbamoyl-1,3-dimethylbarbituric acid,
20.0 parts of tallow fatty amine ethoxylated with 6 to 7 moles of ethylene oxide,
5.0 parts of a block polymer of propylene glycol and ethylene oxide (average mol. wt. 4900; 80% hydrophobic groups, 20% hydrophilic groups; HLB=4),
7.0 parts of castor oil polyglycol ether,
3.0 parts of an alkylphosphoric acid partial ester,
54.5 parts of isophoron (3,5,5-trimethyl-2-cyclohexen-1-one).

In this formulation, cypermethrin may be replaced by permethrin and/or the alkylphosphoric acid partial ester by succinic acid, lactic acid, formic acid or acetic acid.

EXAMPLE 4

A formulation of the following composition is prepared as in Example 1:
5.3 parts of permethrin,
5.0 parts of 5-(3,4-dichlorophenyl)carbamoyl-1,3-dimethylbarbituric acid,
8.0 parts of 1-hydroxyethyl-2-oleylimidazoline,
7.0 parts of tallow fatty amine ethoxylated with 6 to 7 moles of ethylene oxide,
73.7 parts of diethylene glycol ethyl ether,
1.0 parts of lactic acid (racemic).

In this formulation, permethrin may be replaced by cypermethrin, lactic acid by an alkylphosphoric acid partial ester, formic acid, acetic acid, propionic acid or another carboxylic acid, and/or diethylene glycol ethyl ether by dimethyl methylphosphonate, N-methyl-2-pyrrolidone, ethyl polyglycol or a polydiol.

EXAMPLE 5

A formulation of the following composition is prepared as in Example 1:
5.5 parts of cypermethrin,
5.0 parts of 5-(3,4-dichlorophenyl)carbamoyl-1,3-dimethylbarbituric acid,
10.0 parts of dimethyl laurylamine,
15.0 parts of a block polymer of propylene glycol and ethylene oxide (average mol. wt. 4900; 80% hydrophobic groups, 20% hydrophilic groups; HLB=4),
10.0 parts of N-lauryl-N-myristyl-β-aminopropionic acid,
51.5 parts of diethylene glycol ethyl ether,
3.0 parts of succinic acid.

In this formulation, cypermethrin may be replaced by permethrin and/or succinic acid by acetic acid, formic acid, lactic acid or by an alkylphosphoric acid partial ester.

EXAMPLE 6

A formulation of the following composition is prepared as in Example 1:
5.5 parts of permethrin,
5.0 parts of 5-(3,4-dichlorophenyl)carbamoyl-1,3-dimethylbarbituric acid,
12.0 parts of dimethyl laurylamine,
12.0 parts of lauryl polyglycol ether,
5.0 parts of difatty acid isopropyl ester dimethylammonium methosulfate,
10.0 parts of benzyl alcohol,
46.0 parts of isoparaffin,
4.5 parts of lactic acid (racemic).

In this formulation, cypermethrin may be replaced by permethrin and/or lactic acid by succinic acid, formic acid, acetic acid or by an alkylphosphoric acid partial ester.

EXAMPLE 7

A formulation of the following composition is prepared as in Example 1:
5.5 parts of cypermethrin,
5.0 parts of 5-(3,4-dichlorophenyl)carbamoyl-1,3-dimethylbarbituric acid,
5.0 parts of dimethyl laurylamine,
5.0 parts of 1-hydroxyethyl-2-oleoylimidazoline,
9.0 parts of nonylphenol polyglycol ether,
6.0 parts of distearyl dimethylammonium chloride,
10.0 parts of isophoron,
51.5 parts of isoparaffin,
3.0 parts of lactic acid (racemic).

In this formulation, cypermethrin may be replaced by permethrin and/or lactic acid by succinic acid, formic acid, acetic acid or by an alkylphosphoric acid partial ester.

EXAMPLE 8

A formulation of the following composition is prepared as in Example 1:
5.5 parts of cypermethrin,
5.0 parts of 5-(3,4-dichlorophenyl)carbamoyl-1,3-dimethylbarbituric acid,
12.0 parts of dimethyl cocoylamine,
12.0 parts of lauryl polyglycol ether,
5.0 parts of difatty acid isopropyl ester dimethylammonium methosulfate,
10.0 parts of isophoron,
46.0 parts of isoparaffin,
4.5 parts of lactic acid (racemic).

In this formulation, cypermethrin may be replaced by permethrin and/or lactic acid by succinic acid, formic acid, acetic acid or by an alkylphosphoric acid partial ester.

EXAMPLE 9

A formulation of the following composition is prepared as in Example 1:
5.5 parts of permethrin,
5.0 parts of 5-(3,4-dichlorophenyl)carbamoyl-1,3-dimethyl barbituric acid,
10.0 parts of dimethyl cocoylamine,
4.0 parts of castor oil polyglycol ether,
3.0 parts of 2-ethyl-1-hexanol ethoxylated with 5 moles of ethylene oxide,
7.5 parts of stearyl alcohol ethoxylated with 8 to 9 moles of ethylene oxide,
62.7 parts of xylene (mixture of isomers),
2.3 parts of formic acid.

In this formulation, permethrin may be replaced by cypermethrin and/or formic acid by acetic acid, lactic acid, succinic acid or by an alkylphosphoric acid partial ester.

EXAMPLE 10

A formulation of the following composition is prepared as in Example 1:

5.5 parts of permethrin,
5.0 parts of 5-(3,4-dichlorophenyl)carbamoyl-1,3-dimethylbarbituric acid,
5.0 parts of dimethyl cocoylamine,
10.0 parts of tallow fatty amine ethoxylated with 6 to 7 moles of ethylene oxide,
73.0 parts of dimethyl methylphosphonate,
1.5 parts of formic acid.

In this formulation, permethrin may be replaced by cypermethrin and/or formic acid by acetic acid, lactic acid, succinic acid or by an alkylphosphoric acid partial ester.

EXAMPLE 11

A formulation of the following composition is prepared as in Example 1:

5.5 parts of cypermethrin,
5.0 parts of 5-(3,4-dichlorophenyl)carbamoyl-1,3-dimethylbarbituric acid,
10.0 parts of dimethyl cocoylamine,
9.5 parts of octyl phenol polyglycol ether,
67.0 parts of pine oil,
3.0 parts of an alkylphosphoric acid partial ester.

In this formulation, cypermethrin may be replaced by permethrin and/or the alkylphosphoric acid partial ester by succinic acid, lactic acid, formic acid or acetic acid.

EXAMPLE 12

A formulation of the following composition is prepared as in Example 1:

5.5 parts of permethrin or cypermethrin,
5.0 parts of 5-(3,4-dichlorophenyl)carbamoyl-1,3-dimethylbarbituric acid,
30.0 parts of cocoylamine ethoxylated with 5 moles of ethylene oxide,
10.0 parts of a block polymer of propylene glycol and ethylene oxide (average mol. wt. 6350; 50% hydrophobic groups and 50% hydrophilic groups: HLB=15),
10.0 parts of nonyl phenol ether sulfate, sodium salt, ethoxylated with 40 moles of ethylene oxide,
15.0 parts of ethyl polyglycol,
24.5 parts of water; or
5.5 parts of permethrin or cypermethrin,
5.0 parts of 5-(3,4-dichlorophenyl)carbamoyl-1,3-dimethylbarbituric acid,
30.0 parts of cocoylamine ethoxylated with 8 moles of ethylene oxide,
10.0 parts of nonyl phenol ether sulfate, sodium salt, ethoxylated with 40 moles of ethylene oxide,
15.0 parts of ethyl polyglycol,
34.5 parts of water.

EXAMPLE 13

A formulation of the following composition is prepared as in Example 1:

5.5 parts of permethrin or cypermethrin,
5.0 parts of 5-(3,4-dichlorophenyl)carbamoyl-1,3-dimethylbarbituric acid,
20.0 parts of tallow fatty amine ethoxylated with 6 to 7 moles of ethylene oxide,
29.5 parts of ethyl polyglycol,
20.0 parts of nonyl phenol ether sulfate, sodium salt, ethoxylated with 40 moles of ethylene oxide,
20.0 parts of a block polymer of propylene glycol and ethylene oxide (average mol. wt. 6350; 50% hydrophobic and 50% hydrophilic groups; HLB=15), or
5.5 parts of permethrin or cypermethrin,
5.0 parts of 5-(3,4-dichlorophenyl)carbamoyl-1,3-dimethylbarbituric acid,
20.0 parts of tallow fatty amine ethoxylated with 6 to 7 moles of ethylene oxide,
29.5 parts of ethyl polyglycol,
20.0 parts of a block polymer of propylene glycol and ethylene oxide (average mol, wt. 4900; 80% hydrophobic and 20% hydrophilic groups; HLB=4),
20.0 parts of water.

EXAMPLE 14

A formulation of the following composition is prepared as in Example 1:

5.5 parts of permethrin or cypermethrin,
5.0 parts of 5-(3,4-dichlorophenyl)carbamoyl-1,3-dimethylbarbituric acid,
45.0 parts of the compound of the formula

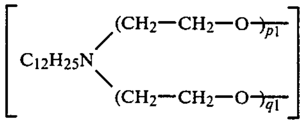 X, wherein $P_1+q_1=8$ and X is an acid phosphoric acid radical,
20.0 parts of a block polymer of propylene glycol and ethylene oxide (average mol. wt. 6350; 50% hydrophobic and 50% hydrophilic groups; HLB=15),
12.5 parts of nonyl phenol ether sulfate, sodium salt, ethoxylated with 40 moles of ethylene oxide,
7.0 parts of ethyl polyglycol,
5.0 parts of polyethylene glycol 300.

EXAMPLE 15

A formulation of the following composition is prepared as in Example 1:

5.5 parts of permethrin or cypermethrin,
5.0 parts of 5-(3,4-dichlorphenyl)carbamoyl-1,3-dimethylbarbituric acid,
30.0 parts of the compound of the formula

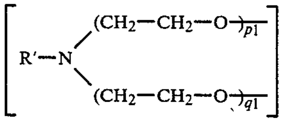 X, wherein $P_1+q_1=8$, X is an acid phosphoric acid radical and R' is the hydrocarbon radical of tallow fatty amine,
10.0 parts of a block polymer of propylene glycol and ethylene oxide (average mol. wt. 4900; 80% hydrophobic and 20% hydrophilic groups; HLB=4),
15.0 parts of ethyl polyglycol,
34.5 parts of water.

EXAMPLE 16

A formulation of the following composition is prepared as in Example 1:

5.5 parts of permethrin or cypermethrin, 5.0 parts of 5-(3,4-dichlorophenyl)carbamoyl-1,3-dimethylbarbituric acid, 40.0 parts of the compound of the formula

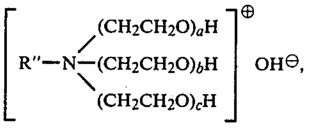

wherein R" is the hydrocarbon radical of a fatty amine and the sum of a+b+c is 10, 10.0 parts of a block polymer of propylene glycol and ethylene oxide (average mol. wt. 6350; 50% hydrophobic and 50% hydrophilic groups; HLB=15), 15.0 parts of ethyl polyglycol, 24.5 parts of water.

The five formulations of the following compositions (Examples 17 to 21) are obtained in corresponding manner to Example 1.

EXAMPLE 17

5.3 parts of permethrin, 5.0 parts of 5-(3,4-dichlorophenyl)carbamoyl-1,3-dimethylbarbituric acid, 1.1 parts of isopropanolamine (1-amino-2-propanol), 5.0 parts of a mixture of the formula

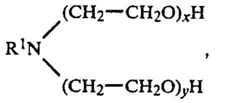

wherein x+y are about 7 and $R^1$ is a mixture of about 30% of $CH_3(CH_2)_{15}$—, about 30% of $CH_3(CH_2)_{17}$— and about 40% of $CH_3(CH_2)_7$—CH=CH—$(CH_2)_8$—, 5.0 parts of a condensation product of ethylenediamine with propylene oxide and ethylene oxide (ratio of propoxy groups to ethoxy groups=90:10; average mol. wt. 6000-6500), 1.0 parts of a condensation product of 2 moles of nonyl phenol with 20 moles of ethylene oxide, esterified with phosphoric acid (di-(nonylphenoldecaglycol ether)phosphate), 73.6 parts of diethylene glycol monomethyl ether, 4.0 parts of water.

EXAMPLE 18

5.3 parts of permethrin, 5.0 parts of 5-(3,4-dichlorophenyl)carbamoyl-1,3-dimethylbarbituric acid, 1.1 parts of isopropanolamine (1-amino-2-propanol), 5.0 parts of a mixture of the formula

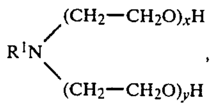

wherein x+y are about 7 and $R^1$ is a mixture of about 30% of $CH_3(CH_2)_{15}$—, about 30% of $CH_3(CH_2)_{17}$— and about 40% of $CH_3(CH_2)_7$—CH=CH—$(CH_2)_8$—, 5.0 parts of a block polymer of propylene glycol and ethylene oxide (average mol. wt. 3500; 90% hydrophobic and 10% hydrophilic groups), 73.6 parts of diethylene glycol monomethyl ether, 5.0 parts of water.

EXAMPLE 19

5.3 parts of permethrin, 5.0 parts of 5-(3,4-dichlorophenyl)carbamoyl-1,3-dimethylbarbituric acid, 2.0 parts of diisopropanolamine (bis-(2-hydroxypropyl-)amine), 3.0 parts of a mixture of the formula

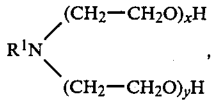

wherein x+y is about 7 and $R^1$ is a mixture of about 30% of $CH_3(CH_2)_{15}$—, about 30% of $CH_3(CH_2)_{17}$— and about 40% of $CH_3(CH_2)_7$—CH=CH—$(CH_2)_8$—, 3.0 parts of a block polymer of propylene glycol and ethylene oxide (average mol. wt. 4900; 80% hydrophobic and 20% hydrophilic groups), 76.7 parts of diethylene glycol monomethyl ether, 5.0 parts of water.

EXAMPLE 20

5.3 parts of permethrin, 5.0 parts of 5-(3,4-dichlorophenyl)carbamoyl-1,3-dimethylbarbituric acid, 1.3 parts of 2-dimethylaminoethanol, 4.0 parts of a mixture of the formula

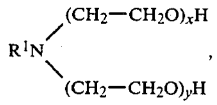

wherein x+y is about 7 and $R^1$ is a mixture of about 30% of $CH_3(CH_2)_{15}$—, about 30% of $CH_3(CH_2)_{17}$ and about 40% of $CH_3(CH_2)_7$—CH=CH—$(CH_2)_8$—, 4.0 parts of a block polymer of propylene glycol and ethylene oxide (average mol. wt. 4900; 80% hydrophobic and 20% hydrophilic groups), 45.4 parts of diethylene glycol monomethyl ether, 5.0 parts of water.

EXAMPLE 21

5.3 parts of permethrin, 5.0 parts of 5-(3,4-dichlorophenyl)carbamoyl-1,3-dimethylbarbituric acid, 4.0 parts of castor oil polyglycol ether, 6.0 parts of ethoxylated 2-ethylhexanol, 8.0 parts of dimethyl cocoylamine, 25.0 parts of piperonyl butoxide, 44.7 parts of xylene (mixture of isomers), 2.0 parts of formic acid.

EXAMPLE 22

A mixture is prepared from 5 parts of permethrin and 90 parts of a propoxylated ethylene diamine with a molecular weight of about 500. With constant stirring, 5 parts of 5-(3,4-dichlorophenyl)carbamoyl-1,3-dimethylbarbituric acid are added to this mixture at about 50° C.

until a homogeneous formulation is obtained. This formulation is storage stable and miscible with water.

EXAMPLE 23

Example 22 is repeated, using instead of 90 parts of propoxylated ethylenediamine with a molecular weight of about 500 a mixture of 45 parts of this latter and 45 parts of a propoxylated ethylenediamine with a molecular weight of about 4000.

EXAMPLES 24 AND 25

The two following formulations are prepared as in Example 22, the 5-(3,4-dichlorophenyl)carbamoyl-1,3-dimethylbarbituric acid being added in each case to the mixture of the other components:

5 parts of permethrin,
5 parts of 5-(3,4-dichlorophenyl)carbamoyl-1,3-dimethylbarbituric acid,
86 parts of a propoxylated ethylenediamine with a molecular weight of about 500,
4 parts of copra acid diethanolamide; and 5 parts of permethrin,
5 parts of 5-(3,4-dichlorophenyl)carbamoyl-1,3-dimethylbarbituric acid,
43 parts of a propoxylated ethylenediamine with a molecular weight of about 500,
43 parts of a propoxylated ethylenediamine with a molecular weight of about 4000,
4 parts of copra acid diethanolamide.

EXAMPLE 26

In the formulations obtained in Examples 1 to 25, the 5-(3,4-dichlorophenyl)carbamoyl-1,3-dimethylbarbituric acid may be replaced by one of the barbiturates of the general formula (A') or thiobarbiturates of the general formula (B') listed in Tables 1 and 2, respectively.

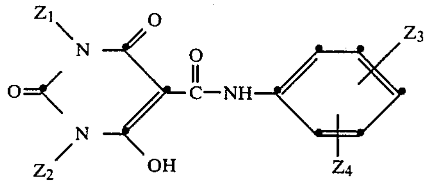

(A')

TABLE 1

| Compound | $Z_1$ | $Z_2$ | $Z_3$ | $Z_4$ | Melting point (°C.) |
|---|---|---|---|---|---|
| 102 | $CH_3$ | $CH_3$ | 2-Cl | 4-Cl | 208-210 |
| 103 | $CH_3$ | $CH_3$ | 4-$CF_3$ | H | 225-227 |
| 104 | $CH_3$ | $CH_3$ | 4-$CF_3$ | H | 188-190 |
| 105 | $CH_3$ | $CH_3$ | 3-$CF_3$ | H | 139-141 |
| 106 | $CH_3$ | $CH_3$ | 3-$CF_3$ | 5-$CF_3$ | 184-185 |
| 107 | $CH_3$ | $CH_3$ | 4-Br | H | 243-245 |
| 108 | $CH_3$ | $CH_3$ | 4-J | H | 254-255 |
| 109 | $CH_3$ | $CH_3$ | 4-F | H | 188-190 |
| 110 | $CH_3$ | $CH_3$ | 3-Cl | 4-Cl | 205-206 |
| 111 | $CH_3$ | $CH_3$ | 4-Cl | 2-$CH_3$ | 179-180 |
| 112 | $CH_3$ | $CH_3$ | 2-Cl | 5-$CF_3$ | 212- |

TABLE 1-continued

| Compound | $Z_1$ | $Z_2$ | $Z_3$ | $Z_4$ | Melting point (°C.) |
|---|---|---|---|---|---|
| | | | | | 213 |
| 113 | $CH_3$ | $CH_3$ | 3-Cl | 4-$CF_3$ | 160-161 |
| 114 | $CH_3$ | $C_2H_5$ | 3-$CF_3$ | 4-Cl | 124-126 |
| 115 | $CH_3$ | $C_2H_5$ | 4-Br | H | 193-195 |
| 116 | $CH_3$ | $C_2H_5$ | 2-Cl | 4-Cl | 133-135 |
| 117 | $CH_3$ | $C_2H_5$ | 3-$CF_3$ | H | 116-118 |
| 118 | $CH_3$ | (i)-$C_3H_7$ | 4-Cl | H | 183-185 |
| 119 | $CH_3$ | (i)-$C_3H_7$ | 2-Cl | 4-Cl | 163-166 |
| 120 | $CH_3$ | (i)-$C_3H_7$ | 4-Br | H | 183-185 |
| 121 | $CH_3$ | (i)-$C_4H_9$ | 4-Br | H | 156-157 |
| 122 | $CH_3$ | (i)-$C_4H_9$ | 2-Cl | 4-Cl | 157-158 |
| 123 | $CH_3$ | (i)-$C_4H_9$ | 3-$CF_3$ | H | 100-102 |
| 124 | $CH_3$ | (i)-$C_4H_9$ | 4-$CF_3$ | H | 115-117 |
| 125 | $CH_3$ | $CH_2=CH-CH_2-$ | 4-Br | H | 124-125 |
| 126 | $CH_3$ | $CH_2=CH-CH_2-$ | 2-Cl | 4-Cl | 143-145 |
| 127 | $CH_3$ | $CH_2=CH-CH_2-$ | 3-$CF_3$ | H | 106-108 |
| 128 | $CH_3$ | $CH_2=CH-CH_2-$ | 4-$CF_3$ | H | 109-111 |
| 129 | $CH_3$ | $CH_3$ | 3-Cl | 5-Cl | |
| 130 | $CH_3$ | $C_2H_5$ | 4-Cl | H | |
| 131 | $C_2H_5$ | (i)-$C_3H_7$ | 4-Cl | H | |
| 132 | $CH_3$ | $CH_2=CH-CH_2-$ | 4-Cl | H | |
| 133 | $C_2H_5$ | $C_2H_5$ | 3-Cl | 4-Cl | |
| 134 | $C_2H_5$ | $C_2H_5$ | 3-$CF_3$ | 4-Cl | |
| 135 | $C_2H_5$ | $C_2H_5$ | 4-Cl | H | 164-166 |
| 136 | $C_2H_5$ | $C_2H_5$ | 2-Cl | 4-Cl | 143-144 |
| 137 | $C_2H_5$ | $C_2H_5$ | 4-Br | H | 170-172 |
| 138 | $C_2H_5$ | $C_2H_5$ | 4-$CF_3$ | H | |
| 139 | $C_2H_5$ | $C_2H_5$ | 3-$CF_3$ | 5-$CF_3$ | |
| 140 | $C_2H_5$ | $C_2H_5$ | 3-Cl | 4-$CF_3$ | |
| 141 | $C_2H_5$ | $C_2H_5$ | 3-$CF_3$ | H | |
| 142 | $C_2H_5$ | $C_2H_5$ | 3-Cl | 5-Cl | |
| 143 | 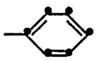 | 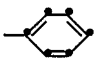 | 3-$CF_3$ | H | 174-175 |
| 144 | 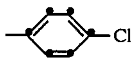 | 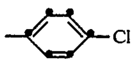 | H | 4-Cl | 229-230 |
| 145 | 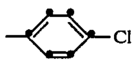 | 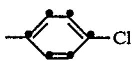 | 3-Cl | 4-Cl | 250-252 |
| 146 | 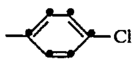 | 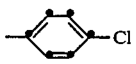 | 3-$CF_3$ | H | 178-179 |
| 147 | 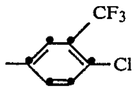 | 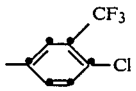 | 3-Cl | 4-Cl | 238-239 |
| 148 | 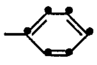 | 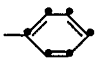 | 4-Cl | H | 218-219 |

TABLE 1-continued

| Compound | $Z_1$ | $Z_2$ | $Z_3$ | $Z_4$ | Melting point (°C.) |
| --- | --- | --- | --- | --- | --- |
| 149 | 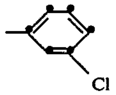 | $CH_3$ | 4-Cl | H | 193–194 |
| 150 | 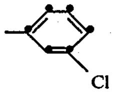 | $CH_3$ | 3-Cl | 4-Cl | 190–191 |
| 151 | 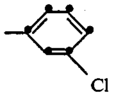 | $CH_3$ | 3-$CF_3$ | H | 171–172 |
| 152 | 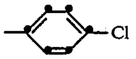 | $CH_3$ | 4-Cl | H | 220–221 |
| 153 | 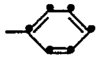 | 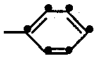 | 3-Cl | 4-Cl | |
| 154 | 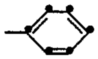 | 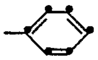 | 4-Cl | 2-Cl | |
| 155 | 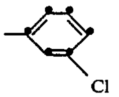 | $CH_3$ | 4-Br | H | |
| 156 | 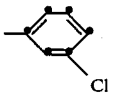 | $CH_3$ | 4-Cl | 2-Cl | |
| 157 | 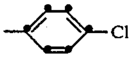 | $CH_3$ | 4-Br | H | |
| 158 | 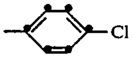 | $CH_3$ | 4-$CF_3$ | H | |
| 159 | 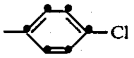 | $CH_3$ | 4-Cl | 3-Cl | |
| 160 | 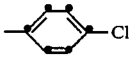 | $CH_3$ | 4-Cl | 2-Cl | |

The two compounds of the formula

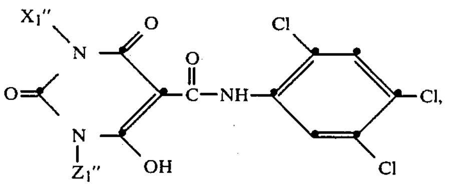

wherein $Z_1''$ is $CH_3$ or $C_2H_5$, may also be used in the formulations, as may also the 5-phenylcarbamoylthiobarbituric acids of the formula

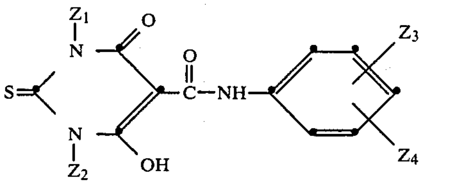

(B')

TABLE 2

| Compound | $Z_1$ | $Z_2$ | $Z_3$ | $Z_4$ | Melting point (°C.) |
| --- | --- | --- | --- | --- | --- |
| 202 | $CH_3$ | $CH_3$ | 4-Cl | H | 243–245 |
| 203 | $CH_3$ | $CH_3$ | 4-Br | H | |
| 204 | $CH_3$ | $CH_3$ | 4-$CF_3$ | H | |
| 205 | $CH_3$ | $CH_3$ | 4-Cl | 3-Cl | |
| 206 | $CH_3$ | $CH_3$ | 4-Cl | 2-Cl | |
| 207 | $CH_3$ | $CH_3$ | 4-Cl | 3-$CF_3$ | |
| 208 | $CH_3$ | $CH_3$ | 4-$CF_3$ | 3-Cl | 185 |
| 209 | $CH_3$ | $CH_3$ | 3-$CF_3$ | H | |
| 210 | $CH_3$ | $CH_3$ | 3-$CF_3$ | 5-$CF_3$ | |
| 211 | $CH_3$ | $CH_3$ | 3-Cl | 5-Cl | |
| 212 | $C_2H_5$ | $C_2H_5$ | 4-Cl | H | |
| 213 | $C_2H_5$ | $C_2H_5$ | 4-Br | H | |
| 214 | $C_2H_5$ | $C_2H_5$ | 4-$CF_3$ | H | 162–165 (triethylammonium salt) |
| 215 | $C_2H_5$ | $C_2H_5$ | 4-Cl | 3-Cl | |
| 216 | $C_2H_5$ | $C_2H_5$ | 4-Cl | 2-Cl | |
| 217 | $C_2H_5$ | $C_2H_5$ | 4-Cl | 3-$CF_3$ | |
| 218 | $C_2H_5$ | $C_2H_5$ | 4-$CF_3$ | 3-Cl | |
| 219 | $C_2H_5$ | $C_2H_5$ | 3-$CF_3$ | H | |
| 220 | $C_2H_5$ | $C_2H_5$ | 3-$CF_3$ | 5-$CF_3$ | |
| 221 | $C_2H_5$ | $C_2H_5$ | 3-Cl | 5-Cl | |
| 222 | $CH_3$ | $C_2H_5$ | 4-Cl | H | |
| 223 | $CH_3$ | $C_2H_5$ | 4-Br | H | |
| 224 | $CH_3$ | $C_2H_5$ | 4-$CF_3$ | H | |
| 225 | $CH_3$ | $C_2H_5$ | 4-Cl | 3-$CF_3$ | |
| 226 | $CH_3$ | i-$C_3H_7$ | 4-Cl | H | |
| 227 | $CH_3$ | i-$C_3H_7$ | 4-Br | H | |
| 228 | $CH_3$ | i-$C_3H_7$ | 4-$CF_3$ | H | |
| 229 | $CH_3$ | i-$C_3H_7$ | 4-Cl | 3-$CF_3$ | |
| 230 | $C_2H_5$ | i-$C_3H_7$ | 4-Cl | H | |
| 231 | $C_2H_5$ | i-$C_3H_7$ | 4-Br | H | |
| 232 | $C_2H_5$ | i-$C_3H_7$ | 4-$CF_3$ | H | |
| 233 | $C_2H_5$ | i-$C_3H_7$ | 4-Cl | 3-$CF_3$ | |
| 234 | $CH_3$ | $CH_3$ | 4-$NO_2$ | 3-Cl | 224–225 |
| 235 | $CH_3$ | $CH_3$ | 4-Cl | 2-$CH_3$ | 206–207 |
| 236 | $CH_3$ | $C_2H_5$ | 4-Cl | 3-Cl | 150–154 |

EXAMPLE 27

In the formulations obtained in Examples 1 to 26, permethrin or cypermethrin may also be replaced by a pyrethroid of the general formula (C')

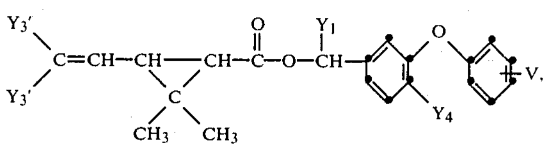

wherein $Y_3'$ is bromine, chlorine or methyl, V is hydrogen, chlorine, bromine, fluorine, methyl, trifluoromethyl or nitro, $Y_4$ is hydrogen or fluorine and $Y_1$ is methyl, ethyl, isopropyl,

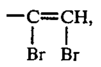

$—C{\equiv}CH$, $—C{\equiv}C—CH_3$, $—CH{=}CH_2$, $—CH{=}CH—CH_3$, $—CH_2—CH{=}CH_2$, $—CH_2—CH{=}CHCl$, $—C{\equiv}C—C_6H_5$ or, if V is different from hydrogen and/or $Y_4$ is fluorine, is also hydrogen or cyano, or by any of the other pyrethroids listed in U.S. Pat. No. 4,283,444 in Example 9.

EXAMPLE 28

Dyeing and simultaneous mothproof and beetle-resistant finish: In a dyeing apparatus, a piece of wool fabric is prewetted for 5 minutes at 40° C. in 600 g of a dye liquor comprising 1.5 g of the formulation of Example 4,
30.3 g of Glauber's salt,
24.0 g of conc. sulfuric acid,
3.0 g of a red dye of the formula

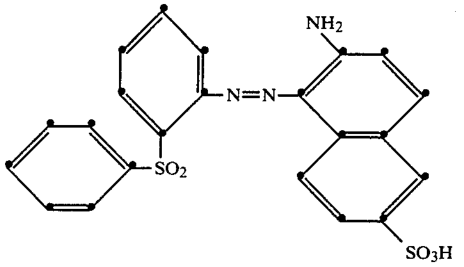

541.5 g of demineralised water.

The liquor to goods ratio is 1:20.

The liquor is then heated over 45 minutes to about 98° C. After it has been treated for 1 hour at this temperature, the wool fabric is rinsed and dried. The dye as well as the barbiturate and permethrin contained in the formulation of Example 4 have exhausted onto the fabric. After this single bath treatment, the red-coloured woollen fabric is fully protected against feeding damage by moths and beetles. This is confirmed by the fastness test according to SNV Standard 195901.

The formulations of Examples 1 to 3 and 5 to 27 may be applied in corresponding manner with the same good exhaust effects and protective action against the larvae of pests that feed on keratin.

EXAMPLE 29

Application by aftertreatment bath:

In a dyeing apparatus, a piece of wool fabric is prewetted for 5 minutes at 30° C. in 400 g of an aftertreatment bath comprising 1 g of the formulation of Example 4,
4 g of 85% formic acid and
395 g of demineralised water.

The liquor to goods ratio is 1:20.

The bath is then warmed over 20 minutes to 45° C. and after it has been treated at this temperature for 30 minutes with constant agitation, the wool fabric is thoroughly rinsed in cold water and dried. The treated fabric is fully protected against the larvae of wool pests.

The formulations obtained according to Examples 1 to 3 and 5 to 27 may be applied in corresponding manner with similarly good exhaust effects and protective action against the larvae of pests that feed on keratin.

What is claimed is:

1. A storage stable mothproofing formulation which comprises

A. 0.5 to 20% by weight of a 5-phenylcarbamoylbarbituric acid compound of the formula

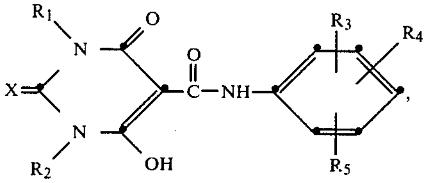

wherein X is oxygen or sulfur, each of $R_1$ and $R_2$ independently of the other is alkyl of 1 to 4 carbon atoms, alkenyl of 3 or 4 carbon atoms, benzyl, phenyl or substituted phenyl, $R_3$ is halogen, nitro or trihalomethyl, $R_4$ is hydrogen, halogen or trihalomethyl, and $R_5$ is hydrogen, halogen, methyl or methoxy, or a tautomer or salt thereof, B. 0.5 to 20% by weight of a synthetic pyrethroid of the formula

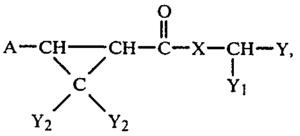

wherein A is $Br_2C{=}CBr—$, 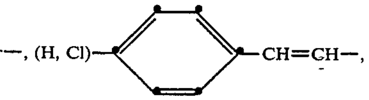

$Cl—C{\equiv}C—$, 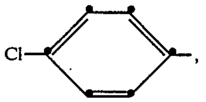

$(CH_3)_3C—O—$, 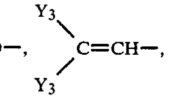

wherein $Y_3$ is Cl, Br, $CF_3$, F or methyl, $CH_2{=}CH—CH_2—O—$ or

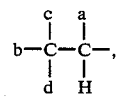

wherein each of a, b, c and d independently of one another is Cl, Br or F, and c and d may also be methyl; X is oxygen or sulfur; $Y_1$ is hydrogen, CN, $CH_3$, $C_2H_5$, $i\text{-}C_3H_7$,

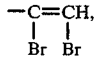

$—C{\equiv}CH$, $—C{\equiv}C—CH_3$, $—C{\equiv}C—C_6H_5$, $—CH{=}CH—CH_3$, $—CH_2—CH{=}CH_2$, $—CH{=}CH_2$ or $={CH_2}—CH{=}CHCl$; $Y_2$ is methyl or both $Y_2$'s together complete a cyclopropane, cyclobutane or cyclopentane ring, and Y is

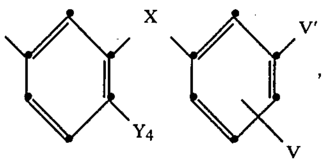

wherein $Y_4$ is hydrogen or fluorine and V is hydrogen, Cl, Br, F, $CH_3$ or $NO_2$, or V' may be $CH_3$ if V is hydrogen, and X is as defined above; and Y is also

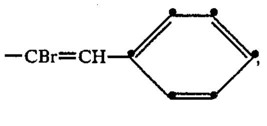

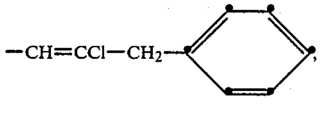

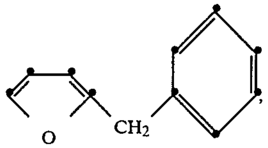

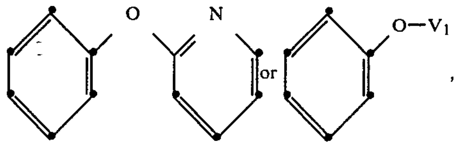

wherein $V_1$ is $-CH_2-CH=CH_2$, $-CH_2-CH\equiv CH$, $-CH_2-CH=CH-CH_3$,

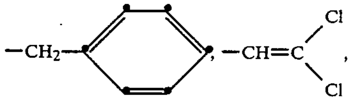

$-CF=CFCl$ or $-CF=CF_2$, and

C. 1 to 90% by weight of one or more fatty amines or cycloaliphatic amines and/or fatty acid amides, or derivatives thereof.

2. A formulation of to claim 1, which comprises
1 to 15% by weight of component A,
1 to 15% by weight of component B, and
5 to 60% by weight of component C.

3. A formulation of either of claims 1 or 2, wherein in component A X is oxygen or sulfur, each of $R_1$ and $R_2$ independently of the other is methyl, ethyl, allyl or a group of the formula

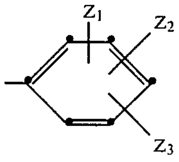

wherein $Z_1$ is hydrogen, chlorine, bromine, methyl, methoxy, ethoxy, $-CF_3$ or nitro, $Z_2$ is hydrogen, chlorine, bromine, methyl or $-CF_3$, $Z_3$ is hydrogen, chlorine or methyl, $R_3$ is chlorine, bromine or $-CF_3$, $R_4$ is hydrogen, chlorine or bromine, and $R_5$ is hydrogen, chlorine, bromine, methyl or methoxy, or a tautomer or salt thereof.

4. A formulation of claim 3, wherein in component A $R_1$ and $R_2$ are methyl, X is oxygen, $R_3$ is trifluoromethyl, chlorine or bromine, $R_4$ is chlorine or hydrogen and $R_5$ is hydrogen.

5. A formulation of either of claims 1 or 2, wherein in component B $Y_1$ is hydrogen, cyano, methyl, $-CH=CH_2-$ or $-CH=CH$; A is $(Y_3)_2$ C=CH— where $Y_3$ is bromine, chlorine or methyl; $Y_2$ is methyl; X is oxygen, and Y is

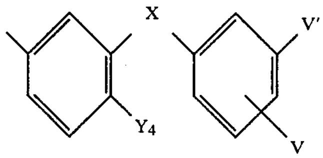

where X is oxygen and $Y_4$, V and $V_1$ are hydrogen.

6. A formulation of either of claims 1 or 2, wherein component C is one or more compounds selected from the following classes: primary, secondary or tertiary fatty amines or amine oxides, quaternised fatty amines, fatty acid amides, alkoxylated fatty acid amides, amino alcohols and alkoxylated amino alcohols, cyclic amines which are substituted by a hydrocarbon radical of 8 to 22 carbon atoms, alkoxylated fatty acid alkylolamides, alkylpropylenediamines and alkoxylated primary, secondary, tertiary and quaternized fatty amines and esters thereof with inorganic acids.

7. A formulation of claim 6, wherein component C is one or more compounds of the following classes: primary, secondary or tertiary fatty amines or amine oxides, quaternised fatty amines, cyclic amines which are substituted by a hydrocarbon radical of 10 to 20 carbon atoms, and alkoxylated primary, secondary or tertiary fatty amines and esters thereof with sulfuric acid or phosphoric acid.

8. A formulation of either of claims 1 or 2, wherein component D is one or more organic solvents of the following classes: aliphatic, cycloaliphatic or aromatic hydrocarbons, aliphatic and alicyclic mono- or polyfunctional alcohols, cyclic or acyclic ketones, chlorinated and fluorinated aliphatic or aromatic hydrocarbons, ethers, formamide, dimethyl formamide, dimethyl methylphosphonate, N-methylpyrrolidone, glycol ethers, polyethylene glycols, ethylene glycol monoalkyl ethers, di- or triethylene glycol alkyl ethers, ethyl polyglycols, polydiols and vegetable oils.

9. A formulation of claim 8, wherein the solvent is dimethyl methylphosphonate, acetoxy-2-ethoxyethane, N-methylpyrrolidone, ethylene glycol, mono-, di-, tri- or polyethylene glycol ethyl ethers or a mixture thereof, isoparaffin, isophoron, benzene, xylene, toluene, naphtha, a polydiol and pine oil or a mixture of such solvents.

10. A formulation of either of claims 1 or 2, wherein component F is one or more compounds of the following classes: block polymers of propylene glycol and ethylene oxide, polyglycol ethers of higher fatty alcohols, ethoxylated alkylphenols and esters thereof with acids, ethoxylated fatty alcohols, ethoxylated cyclic alcohols, alkylphosphoric acid partial esters, N,N-dialkylaminocarboxylic acids and polyethylene glycol.

11. A formulation of either of claims 1 or 2, wherein component G is a saturated or unsaturated monocarboxylic acid, dicarboxylic acid or hydroxymono- or hydroxydicarboxylic acid or a mixture of such acids, preferably formic acid, acetic acid, propionic acid, butyric acid, valeric acid and long chain monocarboxylic acids, oxalic acid, malonic acid, maleic acid, fumaric acid, glutaric acid, adipic acid, tartaric acid, malic acid, citric acid, succinic acid or lactic acid.

12. A formulation of either of claims 1 or 2, wherein in component

A, X is oxygen, $R_3$ is $CF_3$, Cl or Br, $R_4$ is Cl or hydrogen, $R_5$ is hydrogen and $R_1$ and $R_2$ are the same; in component B, $Y_1$ is hydrogen, cyano, methyl, $-CH=CH_2-$ or $-CH=CH$; A is $(Y_3)_2C=CH-$ where $Y_3$ is bromine, chlorine or methyl; $Y_2$ is methyl; X is oxygen; and Y is

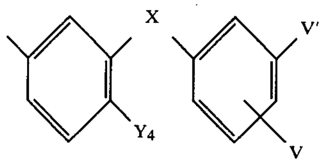

where X is oxygen and $Y_4$, V and $V^1$ are hydrogen; and component

C is a primary, secondary or tertiary fatty amine or fatty amine oxide, a free or ethoxylated fatty acid amide, a quaternary fatty amine, a cyclic amine which is substituted by a $C_8$-$C_{22}$alkyl or $C_8$-$C_{22}$alkenyl group, an ethoxylated fatty acid alkylolamide, an alkylpropylenediamine, an ethoxylated amino alcohol or an ethoxylated primary, secondary, tertiary or quaternary fatty amine, or of a mixture of several of the above nitrogen-containing compounds.

13. A formulation of claim 12, wherein in component A $R_1$ and $R_2$ are methyl, and $R_3$ is chlorine; in component B, $Y_1$ is hydrogen or cyano and $Y_3$ is chlorine; and component C is a primary, secondary or tertiary fatty amine or a fatty amine oxide, a quaternary fatty amine, a 1-($C_1$-$C_4$)alkyl- or -($C_1$-$C_4$)hydroxyalkyl-2-($C_8$-$C_{22}$)alkyl- or -($C_8$-$C_{22}$)alkenylimidazoline or an ethoxylated fatty amine of the formula (8) or (9), or a mixture of several of the above nitrogen-containing compounds; and wherein component A is present to the extent of 1-10% by weight, component B is present to the extent of 1-10% by weight, and component C is present to the extent of 10-50% by weight.

14. A formulation according to either of claims 1 or 2, which additionally contains piperonyl butoxide.

15. A method of protecting keratinous material, in particular wool textiles, from attack by pests that feed on keratin, which method comprises preparing a treatment bath by diluting an effective amount of a formulation as claimed in claim 1, to which bath there may be added further conventional textile auxiliaries and/or dyes, and impregnating the material to be protected with said bath.

16. A method according to claim 15, wherein an aqueous treatment bath is prepared from the formulation.

17. A method according to claim 16, wherein wool textiles are treated with the bath by the exhaust process or by the pad process.

18. A method according to claim 15, wherein the treatment bath is prepared by diluting 0.005 to 200 g of formulation to 1 liter.

19. A method according to claim 17, wherein wool textiles are treated in the dyebath by the exhaust process.

20. A method according to claim 17, wherein the wool textiles are treated in the aftertreatment bath by the exhaust process.

21. A formulation of claim 1, which further comprises one or more of the following components:

D. Up to 80% by weight of one or more organic solvents,

E. Up to 40% by weight of water, provided the organic solvent D is present and is miscible with water, F. Up to 30% by weight of one or more surfactants and/or emulsifiers or dispersants which differ from component C, and G. Up to 10% by weight of one or more aliphatic carboxylic acids.

22. A formulation of claim 21 wherein component D is present to the extent of 15 to 75% by weight.

23. A formulation of claim 7 wherein component C is of the formula

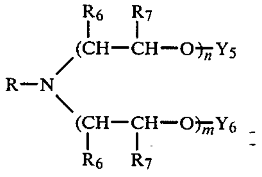

wherein r is a $C_8$-$C_{22}$alkyl or $C_8$-$C_{22}$alkenyl radical, each of $R_6$ and $R_7$ independently of the other is hydrogen or methyl, the sum of n+m is an integer from 2 to 50, and each of $Y_5$ and $Y_6$ independently of the other is hydrogen or the $-SO_3M$ group, in which M is hydrogen or an alkali metal ion or ammonium ion.

24. A formulation of claim 7, wherein component C is of the formula

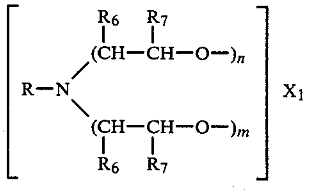

or the alkali metal salts, ammonium salts or amine salts thereof, wherein R is a $C_8$-$C_{22}$alkyl or $C_8$-$C_{22}$alkenyl radical, each of $R_6$ and $R_7$ independently of the other is hydrogen or methyl, and $X_1$ is the acid radical of phosphoric acid, the acid hydrogen atoms of which radical may be replaced by alkali metal ions, ammonium ions or amine salt ions.

25. A formulation of claim 22 and further comprising at least one of the following components:

E. Up to 40% of water provided component D is a water-miscible organic solvent,

F. Up to 15% of a surfactant and or emulsifier and/or dispersant different from C or of a mixture of several of such compounds, G. Up to 5% of saturated or unsaturated mono- or dicarboxylic and or hydroxymono- or hydroxydicarboxylic acid.

26. A formulation of claim 13 and further comprising one or more of the following components:

D. 15 to 75% of one or more solvents selected from the group consisting of dimethyl methylphosphate, acetoxy-2-ethoxyethane, N-methylpyrrolidone, ethylene glycol, mono-, di-, tri- and polyethylene glycol ethyl ethers and mixtures thereof, isoparaffins, isophorone, benzene, xylene, toluene, naphtha, polydiols and pine oil, E. Up to 40% of water, provided component D is a water-miscible solvent, F. Up to 15% of a surfactant, dispersant or emulsifier selected from the group consisting of: block copolymers of propylene glycol and ethylene oxide, polyglycol ethers of higher fatty alcohols, ethoxylated alkylphenols and esters thereof with acids, ethoxylated fatty alcohols, ethoxylated cyclic alcohols, alkylphosphoric acid partial esters, N,N-dialkylaminocarboxylic acids and polyethylene glycol, and G. Up to 5% of a carboxylic acid selected from the group consisting of formic acid, acetic acid, propionic acid, butyric acid, valeric acid and long chain monocarboxylic acids, oxalic acid, malonic acid, maleic acid, fumaric acid, glutaric acid, adipic acid, tartaric acid, maleic acid, citric acid, succinic acid and lactic acid.

* * * * *

UNITED STATES PATENT AND TRADEMARK OFFICE

CERTIFICATE OF CORRECTION

PATENT NO. : 4,502,861

DATED : March 5, 1985

INVENTOR(S) : Carl Becker and Fritz Heizler

It is certified that error appears in the above-identified patent and that said Letters Patent is hereby corrected as shown below:

Claim 2, Column 27, Line 52 should read--

A formulation of claim 1, which comprises --.

Claim 23, Column 30, Line 39 should read-- wherein R is a $C_8$-$C_{22}$alkyl or $C_8$-$C_{22}$alkenyl radical, --.

Signed and Sealed this

*Nineteenth* Day of *November 1985*

[SEAL]

*Attest:*

DONALD J. QUIGG

*Attesting Officer* *Commissioner of Patents and Trademarks*

UNITED STATES PATENT AND TRADEMARK OFFICE
CERTIFICATE OF CORRECTION

PATENT NO. : 4,502,861

DATED : March 5, 1985

INVENTOR(S) : Carl Becker and Fritz Heizler

It is certified that error appears in the above-identified patent and that said Letters Patent is hereby corrected as shown below:

Claim 1, Column 27, Line 13 should read-- gen, Cl, Br, F, $CH_3$ or $NO_2$, or V' may be $CF_3$ if V is --.

Signed and Sealed this

*Seventeenth* Day of *December 1985*

[SEAL]

*Attest:*

DONALD J. QUIGG

*Attesting Officer* *Commissioner of Patents and Trademarks*